United States Patent [19]

Hayashi

[11] Patent Number: 5,432,596
[45] Date of Patent: Jul. 11, 1995

[54] LENS MEASUREMENT APPARATUS PROVIDING MEASUREMENTS OF MULTIPLE LENS CHARACTERISTICS

[75] Inventor: Akihiro Hayashi, Toyokawa, Japan

[73] Assignee: Nidek Co., Ltd., Aichi, Japan

[21] Appl. No.: 82,965

[22] Filed: Jun. 29, 1993

[30] Foreign Application Priority Data

Jun. 30, 1992 [JP] Japan .................... 4-197521

[51] Int. Cl.6 ........................... G01B 11/03
[52] U.S. Cl. ........................ 356/124; 356/127
[58] Field of Search .............. 356/124, 125, 124.5, 356/126, 127, 359, 360, 356, 357, 358

[56] References Cited

U.S. PATENT DOCUMENTS

| 3,614,214 | 10/1971 | Cornsweet et al. | 356/124 |
| 3,639,041 | 2/1972 | Cornsweet | 356/124 |
| 4,410,268 | 10/1983 | Tamaki | 356/124 |
| 4,666,269 | 5/1987 | Nakamura et al. | 351/212 |
| 4,795,250 | 1/1989 | Nakamura et al. | 351/212 |

FOREIGN PATENT DOCUMENTS

| 0139636 | 8/1982 | Japan | 356/124 |
| 60-17335 | 1/1985 | Japan . | |
| 0208736 | 8/1988 | Japan | 356/124 |
| 3-222936 | 10/1991 | Japan . | |
| 0204032 | 7/1992 | Japan | 356/124 |

Primary Examiner—Robert P. Limanek
Assistant Examiner—Alexander Oscar Williams
Attorney, Agent, or Firm—Finnegan, Henderson, Farabow, Garrett & Dunner

[57] ABSTRACT

Lens measurement apparatus provides a holding device for holding a lens to be measured at a designated position, a first index projecting optical system for projecting a first refractive power measuring index onto the lens, a second index projecting optical system for projecting a second radius of curvature measuring index onto the concave surface thereof. A refractive power and a radius of curvature are obtained by arranging a light splitting member on the optical path of the first index luminous flux, or by moving a photoelectric detecting element for detecting each position of the first index and the second index along with the optical axis.

10 Claims, 5 Drawing Sheets

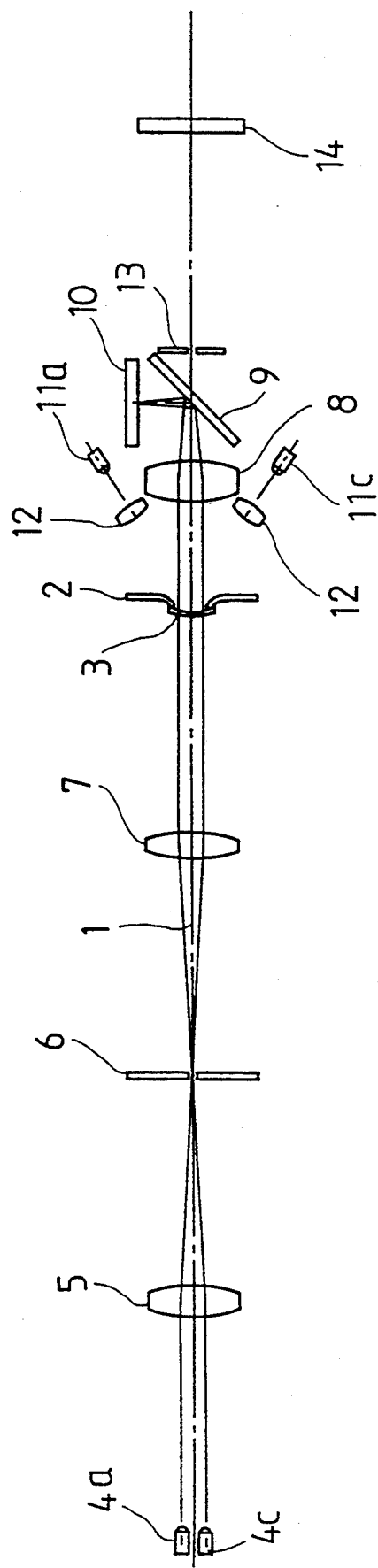

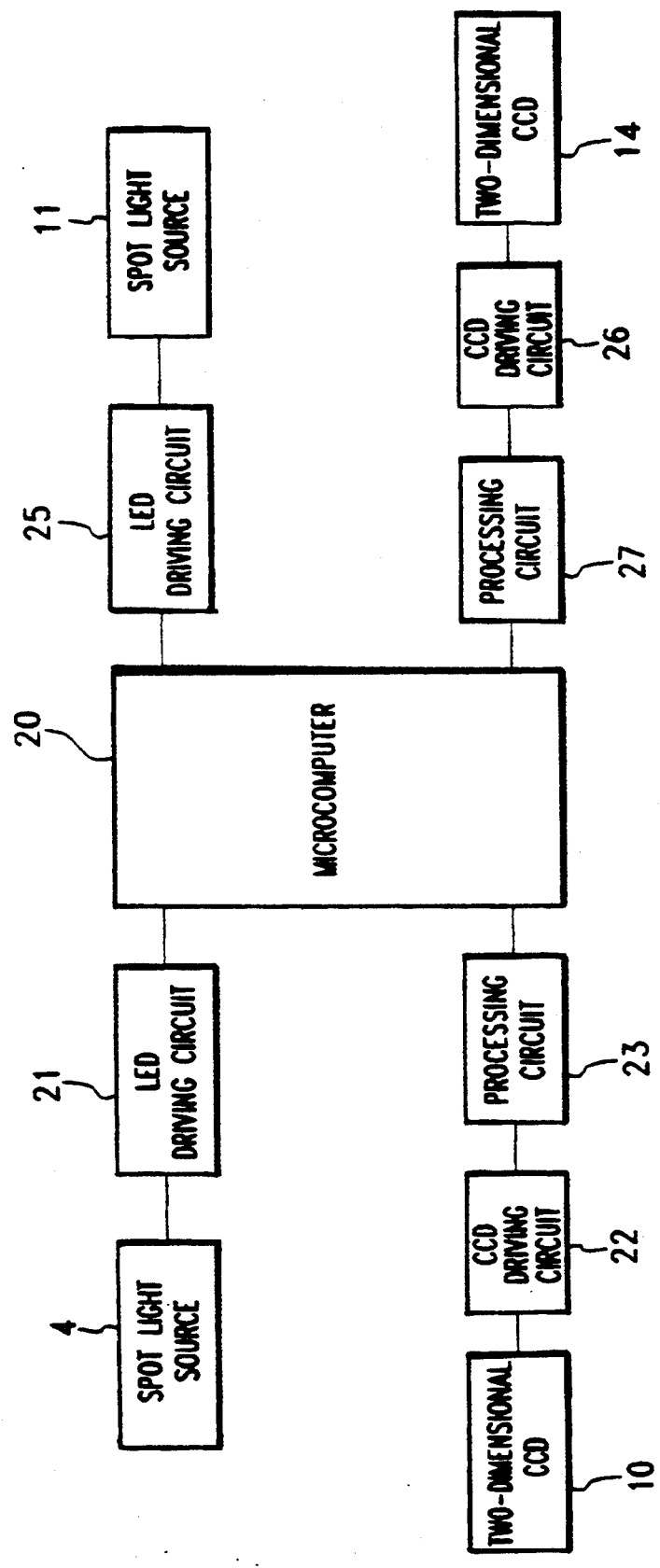

LENS MEASUREMENT APPARATUS PROVIDING MEASUREMENTS OF MULTIPLE LENS CHARACTERISTICS

BACKGROUND OF THE INVENTION

1. Field of the Invention

The present invention relates to a lens measurement apparatus, and more particularly to a lens measurement apparatus suitable for measurement of lens characteristic including radius of curvature and refractive power of contact lens.

2. Description of Related Art

Selection elements of contact lens are usually refractive power, and radius of curvature of back surface of contact lens. And individual measurement apparatuses are conventionally used to measure the above elements of contact lens, that is, lensmeter for refractive power and radius gage for radius of curvature.

Owing to necessity of using the two different type apparatuses according to each measurement element, it takes a long time and also costs highly to measure the characteristic of contact lens.

SUMMARY OF THE INVENTION

The present invention has been made in view of the above circumstances and has an object to overcome the above problems and to provide a lens measurement apparatus, with which the measurement of characteristic of contact lens including refractive power and radius of curvature need not a long time, and the cost being also reasonable.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a lens measurement apparatus of this invention comprises a holding means for holding a lens to be measured at a designated position, a first index projecting optical system for projecting a first index onto the lens, the first index being for measurement of refractive power of the lens, a first detecting optical system for detecting a position of the first index transmitted through the lens with a first photoelectric detecting element, a refractive power processing means for processing the refractive power of the lens based on the detected data of the first photoelectronic detecting element, a second index projecting optical system for projecting a second index onto the concave surface thereof, the second index being for measurement of radius of curvature of the lens, a light splitting member arranged on the optical path of the first index luminous flux, a second detecting optical system, diverging from the optical path of the first index through the light splitting member, for detecting the second index image reflected by the lens with the second photoelectronic detecting element, and a radius of curvature processing means for processing the radius of curvature of the concave surface of the lens based on the detected-data of-the second photoelectronic detecting element.

In the second aspect of the present invention, a lens measurement apparatus comprises a holding means for holding a lens at a designated position, a first index projecting optical system for projecting a first index onto the lens, the first index being for measurement of refractive power of the lens, a second index projecting optical system for projecting a second index onto the concave surface of the lens, the second index being for measurement of radius of curvature of the lens, a detecting optical system for detecting each position of the first index and the second index through a photoelectric detecting element, a measurement mode changing means for changing the first measurement mode for projecting the first index onto the lens into the second measurement mode for projecting the second index onto the lens, a moving means for moving a detecting position of the photoelectric detecting element along the optical axis based on mode changing signal of the measurement mode changing means, and a processing means for determining the refractive power of the lens based on the detected position of the first index and the radius of curvature of the lens based on the detected position of the second index through the photoelectric detecting element.

According to the present invention, the refractive power and the radius of curvature of the contact lens set on a designated position can be simultaneously or sequentially measured, thereby the measurement operation may become simple and the cost may become reasonable.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings, FIG. 1 a schematic diagram of arrangement of optical system in a first embodiment of the present invention, and showing the measurement of refractive power of contact lens;

FIG. 2 a schematic diagram of arrangement of optical system in the first embodiment, and showing the measurement of radius of curvature of contact lens;

FIG. 4 a control block diagram explaining the operation of the lens measurement apparatus of FIGS. 1 and 2;

DETAILED DESCRIPTION OF THE PREFERRED EMBODIMENTS

A detailed description of one preferred embodiment of a measurement apparatus embodying the present invention will now be given referring to the accompanying drawings.

Figure 3:
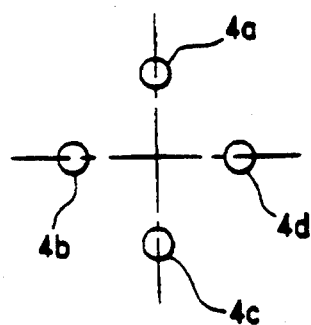
FIG. 3 is a schematic diagram of arrangement of four point light sources 4a–4d for measurement of refractive power in the lens measurement apparatus of FIGS. 1 and 2.

FIGS. 1, 2, and 3 show an arrangement of optical system of a lens characteristic measurement apparatus of a first embodiment.

Refractive power measuring system comprises, on an optical axis 1, a holding table 2 on which a contact lens 3 to be measured is to be put, four point light sources 4a, 4b, 4c and 4d located in a solid reference plane transverse to the axis 1 (see FIGS. 1 or 2 and 3) at a convex surface side of the lens 3, lenses 5 and 7, a spot diaphragm 6, a focussing lens 8, a beamsplitter 9 and a two-dimensional CCD 10 arranged conjugately with the spot diaphragm 6 to the lens 7 and the focussing lens 8. At a front focus point of the lens 5, the four point light sources 4a–4d (light source 4b and 4d would be out of the plane of the drawing sheet and are shown only in FIG. 3 to simplify FIGS. 1 and 2) are arranged respectively apart from the optical axis 1 by equal distance as shown in FIG. 3, thereby the measurement luminous flux emitted from the point light sources 4a–4d will become parallel luminous flux through the lens 5. As shown in FIG. 3, four point light sources are utilized for the measurement in this embodiment, at least three point light sources enabling the lens measurement. The spot diaphragm 6 is disposed at a position being a back focus point of the lens 5 and a front focus point of the lens 7, and the lens 7 is disposed at a position where its back focus point agrees approximately with an apex of the contact lens 3.

In the above optical the light luminous flux, parallel to the optical axis, emitted from the four point light sources 4a–4d are passed through the spot diaphragm 6, and focused on the approximate apex of contact lens 3 through the lens 7.

Figure 8:
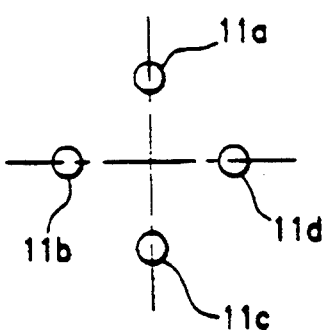
FIG. 8 is a schematic diagram of an arrangement of four point light sources 11a–11d for measurement of radius lens curvature in the lens measurement apparatus of FIGS. 1 and 2.

Radius of curvature measuring system comprises, at a concave surface side of the lens 3, four point light sources 11a, 11b, 11c and 11d located in a solid reference plane transverse to the axis 1 and arranged respectively at a designated angle to and by equal distance from the optical axis 1 (see FIGS. 1 or 2 and FIG. 8), a collimator lens 12 through which the luminous flux emitted from the point light sources 11a–11d become parallel luminous flux, a diaphragm 13 of telecentric mechanism disposed at a focus point of the focussing lens 8 and a two-dimensional CCD 14 disposed at a conjugate position with F-point described below to the focussing lens 8. Emitted from the four light sources 11a–11d (light sources 11b and 11d would be out of the plan of the drawing sheet and are shown only in FIG. 8 to simplify FIGS. 1 and 2), the parallel luminous flux goes toward the contact lens 3, the projecting optical axis of which passing through F-point distant from the contact lens 3 by about 3.9 mm (a focus point of contact lens having an average radius of curvature).

Referring to FIG. 4, each measurement of contact lens is achieved by utilizing the above mentioned apparatus.

In refractive power measurement mode, microcomputer 20 turn on the four point light sources 4a–4d in sequence through LED driving circuit 21 to illuminate the spot diaphragm 6. The luminous flux from the four point light sources 4a–4d transmit through the spot diaphragm 6, the lens 7, the contact lens 3 on the holding table 2 and the focussing lens 8, and is reflected by the beamsplitter 9 toward the two-dimensional CCD 10. If the contact lens 3 has no refractive power then, the luminous flux through the lenses 7 and 8, reflected by the beamsplitter 9 is focused on the two-dimensional CCD 10 along the optical axis.

If the contact lens 3 has refractive power alternatively, the image of the spot diaphragm 6 is projected separately into four images on the two-dimensional CCD 10, four images which are respectively positioned according to the refractive power of the contact lens 3. The image information on the two-dimensional CCD 10 is fetched by a CCD driving circuit 22, and further converted into digital signal indicating each center position of four images through a processing circuit 23.

Based on the digital signal showing four points, the microcomputer 20 finds out spherical refractive power, cylindrical refractive power, astigmatic axis and prism power. The calculating operation thereof is commonly known, the applicant of the present invention have also disclosed in Japanese Laid-Open Patent No. SHO 60(1985)-17335 entitled "Auto-Lens Meter", thereby the detail description is omitted in this specification.

And the calculated measurement data is stored in a memory of the microcomputer 20 by pressing a memory button of the lens measurement apparatus.

Stored the measurement data concerning the refractive power of the contact lens 3, microcomputer 20 changes automatically the measurement mode to radius of curvature measurement mode, turning on four point light sources 11a, 11b, 11c and 11d in sequence or at once. The luminous flux emitted from four point light sources 11a–11d are transmitted through each collimator lens 12 toward the back surface of the contact lens 3, and reflected by the contact lens 3. The respective reflected luminous flux are focused at a half position of the radius of curvature of the contact lens 3 (at approximately F-point), so that respective images $i_a$, $i_b$, $i_c$ and $i_d$ of the point light source 11a–11d are formed at the position. The distance of images from the optical axis varies according as the back radius of curvature of the contact lens 3.

The luminous flux of the images $i_a$–$i_d$, parallel to the optical axis, are fetched out as a principal ray for measurement through a telecentric optical system consisted of the focussing lens 8 and a diaphragm 13, and then each position of the images $i_a$–$i_d$ are detected by a two-dimensional CCD 14. The detected data are processed at a processing circuit 27 through a CCD driving circuit 26, so that each position of the images is found as digital signal. Based on the digital signals indicating each position of the images, the microcomputer 20 finds out the back radius of curvature of contact lens 3.

A calculating process to find the radius of curvature has been proposed by the applicant of the present invention in Japanese Laid-Open Patent No.HEI 3(1991)-222936 which is filed in, the United States (U.S. application Ser. No. 646,908) entitled "Apparatus for measuring cornea shape", thereby the detail description is omitted.

In the present embodiment, LED or similar devices are utilized for each emission wavelength of the point light source 4a and the point light source 11a, the beamsplitter 9 is accordingly used. But also, with different emission wavelength for the point light source 4a and the point light source 11a respectively, a dichroic mirror instead of the beamsplitter 9 or a wavelength splitting filter on the optical path can be used, thereby simultaneous measurement of the refractive power and the radius of curvature may be achieved.

Figure 5:
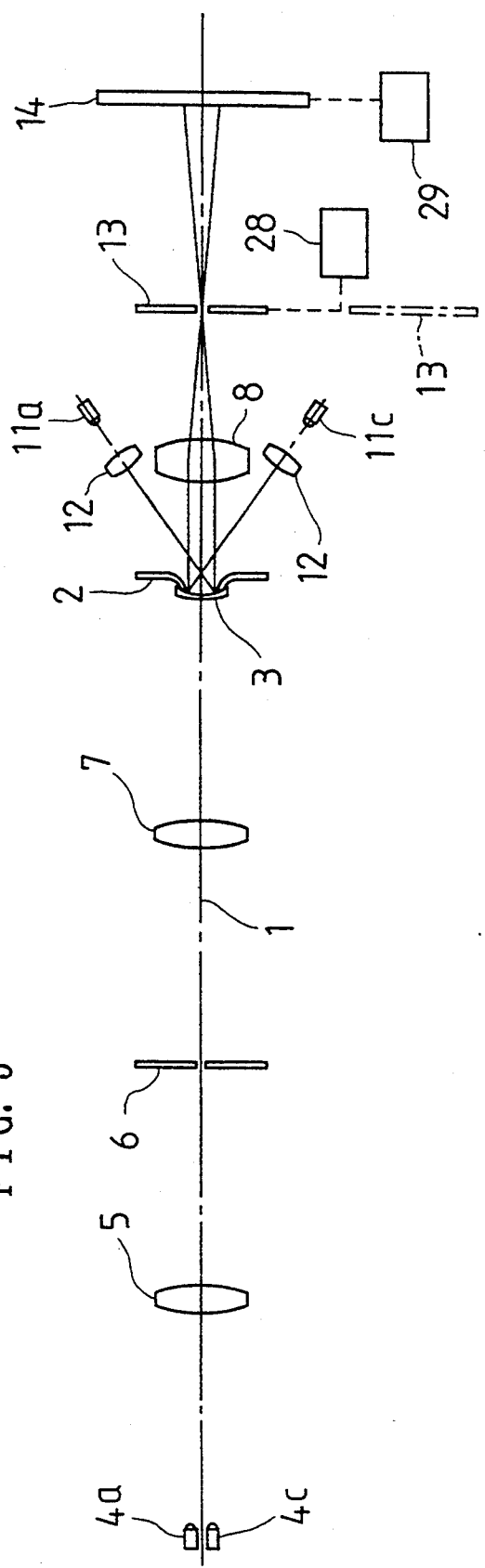
FIG. 5 schematic diagram of arrangement of optical system in a second embodiment of the present invention, and showing the measurement of radius of curvature of contact lens.
Figure 6:
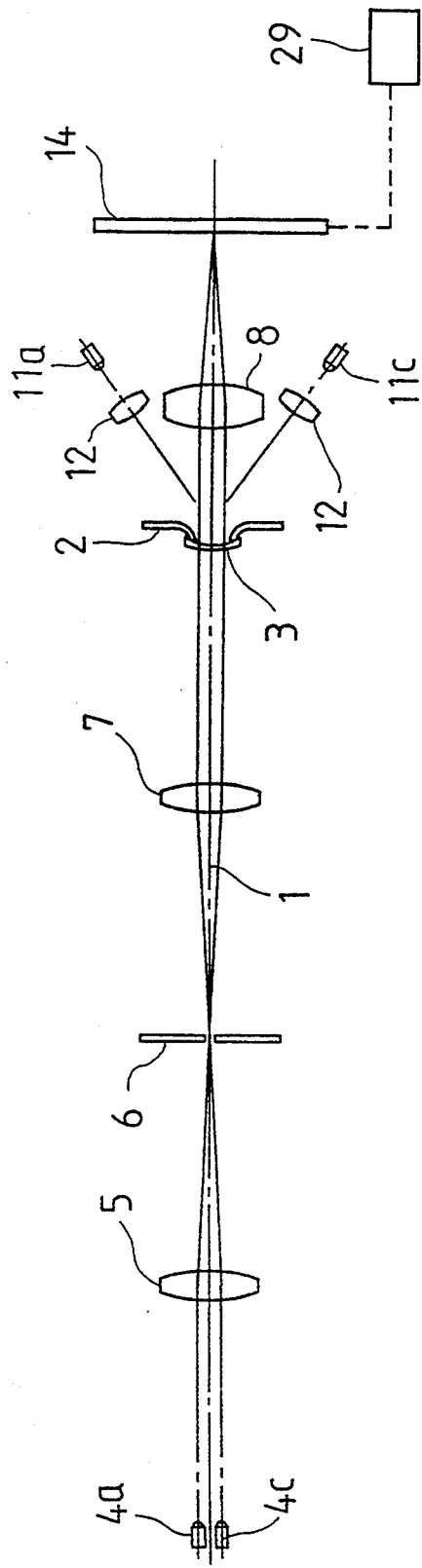
FIG. 6 a schematic diagram of arrangement of optical system in the second embodiment, showing the measurement of refractive power of contact lens.

FIGS. 5 and 6 show an arrangement of optical system of the lens characteristic measurement apparatus in the second embodiment of the present invention. In the second embodiment, a photodetector (two-dimensional CCD) is used in common for the refractive power measuring system and the radius of curvature measuring system, and the same member as the first embodiment mentioned above is numbered the same number.

As shown in FIGS. 5 and 6, the apparatus of the second embodiment comprises further a motor 28 for moving a telecentric diaphragm onto or out of the optical axis 1 and a motor 29 for moving a two-dimensional CCD 14 along the optical axis 1.

Figure 7:
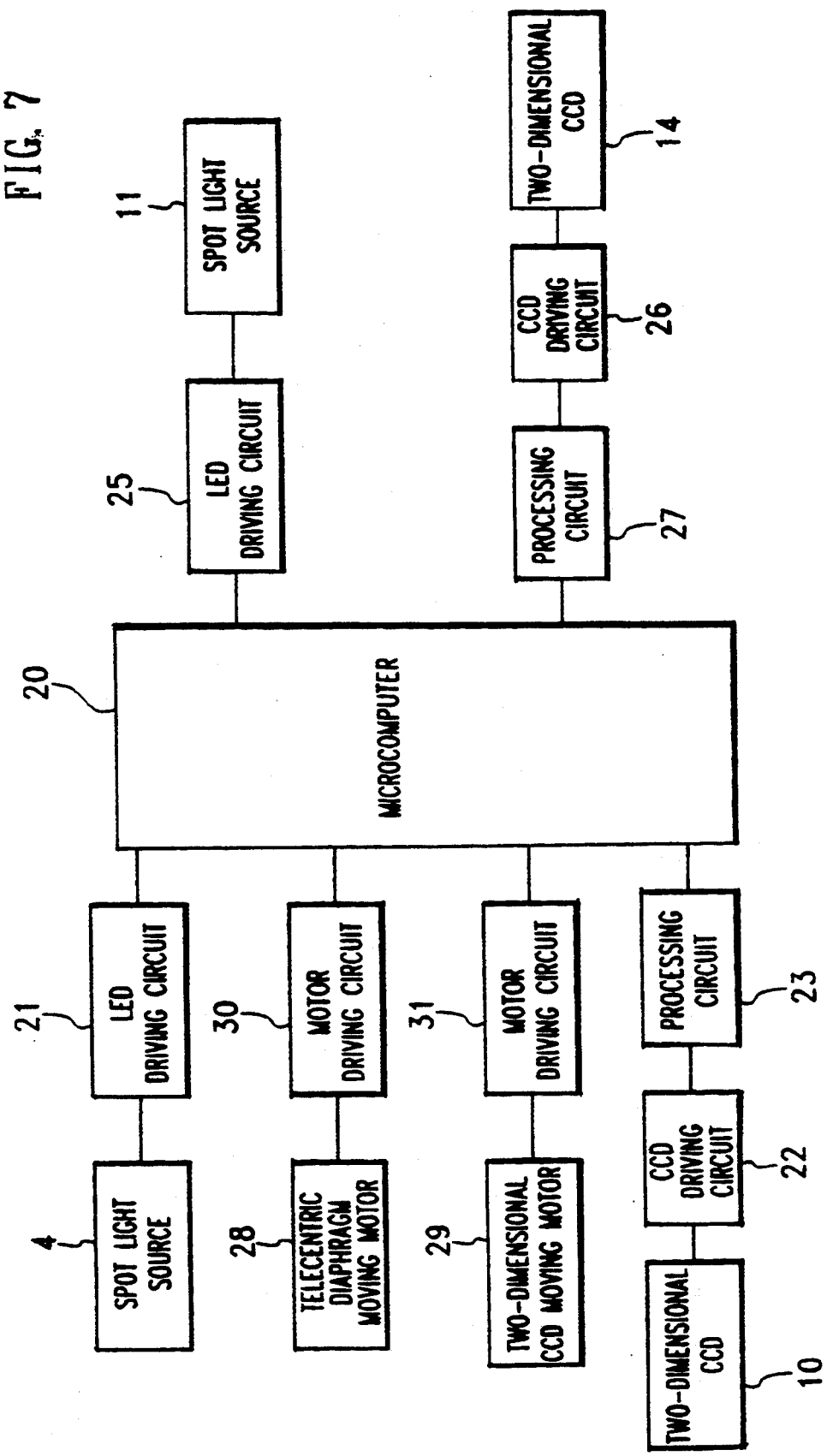
FIG. 7 is control block diagram explaining the operation of the lens measurement apparatus of FIGS. 5 and 6.

When changed to the refractive power measurement mode with a mode selecting button not shown or automatically, the microcomputer 20 works, referring to FIG. 7 showing the control block diagram, the motor 28 through a motor driving circuit 30 so that a diaphragm 13 is moved out of the optical path 1, and simultaneously the motor 29 through a motor driving circuit 31 so that a two-dimensional CCD 14 is moved to a conjugate point with a diaphragm 6 along the optical axis 1. Expecting the motors 28 and 29, FIG. 7 shows the same as FIG. 4, the detail explanation thereof is omitted.

In the above apparatus, the two-dimensional CCD 14 can be therefore in common used for both measuring system; refractive power measuring system and radius of curvature measuring system, and thereby the beam-splitter 9 may be omitted.

The present invention may be embodied in other specific forms without departing from the spirit or essential characteristics thereof. For instance, the same result may be obtained by using ring-shaped light source instead of point light source, and by measuring two-dimensionally with a plural of one-dimensional element as photoelectronic device.

With adequately smaller point light sources 4a–4d and spot diaphragm 6, the refractive power of contact lens can be precisely measured, even if the spot diaphragm 6 is not disposed at a conjugate position with the photodetecting element.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. Lens measurement apparatus comprising:
   holding means for holding a lens to be measured at a designated position;
   a first index projecting optical system for projecting a first index onto the lens, the first index being for measurement of refractive power of the lens;
   a first detecting optical system for detecting a position of the first index transmitted through the lens with a first photoelectric detecting element;
   refractive power processing means for processing the refractive power of the lens based on the detected data of the first photoelectronic detecting element;
   a second index projecting optical system for projecting a second index onto the concave surface thereof, an optical path of the second index projecting optical system intersecting an optical path of the first detecting optical system just short of a concave surface of the lens, the second index being for measurement of radius of curvature of the lens;
   a light splitting member arranged on the optical path of said first index luminous flux;
   a second detecting optical system, diverged from the first detecting optical system by the light splitting member, for detecting a position of the second index image reflected by the lens with the second photoelectronic detecting element; and
   radius of curvature processing means for processing the radius of curvature of the concave surface of the lens based on the detected data of said second photoelectronic detecting element.

2. Lens measurement apparatus according to claim 1, wherein the luminous flux of said first index and same of said second index have different wavelength each other, said light splitting member reflects luminous flux of one index and transmits same of another index according to the wavelength of luminous flux.

3. Lens measurement apparatus according to claim 1, wherein said first index projecting optical system comprises four light sources on a same circle centering the optical axis.

4. Lens measurement apparatus according to claim 1, wherein said second index projecting optical system comprises an optical system for projecting at least three point light sources onto the lens, the point light sources being arranged on a same circle centering the optical axis of the second detecting optical system.

5. Lens measurement apparatus comprising:
   holding means for holding a lens at a designated position by supporting the concave surface of the lens;
   a first measurement light source for measurement of refractive power of the lens, arranged apart from the optical axis by equal distance;
   an index for measurement of refractive power to be illuminated with said first measurement light source;
   a first detecting optical system for forming the image of the first index on a first photoelectric detecting element for detecting two-dimensional position thereof, and thereby detecting the position of the image;
   refractive power processing means for processing the refractive power of the lens based on the detected data by said first detecting optical system;
   concave surface reflecting image forming means comprising a collimating lens and a second measurement light source for projecting at least three parallel luminous flux onto the concave surface of the lens, the parallel luminous flux being arranged at respective designated angles to the optical axis of the first detecting optical system onto the concave surface of the lens, and an optical path of the luminous flux intersecting an optical path of the first detecting optical system approximately at an focal point of the concave surface;
   telecentric diaphragm arranged on the optical path which is in common used for the first detecting optical system and a focusing lens and diverged from the first detecting optical system by a light splitting mirror, also at a focus point of the focusing lens;

second detecting optical system for forming the concave surface reflected image on the second photoelectric detecting element for detecting the two-dimensional position thereof, and thereby detecting the position of the image; and radius of curvature calculating means for calculating the radius of curvature of concave surface of the lens based on the detected data by the second detecting optical system.

6. Lens measurement apparatus comprising:

a holding means for holding a lens at a designated position;

a first index projecting optical system for projecting a first index onto the lens, the first index being for a first mode of measurement of refractive power of the lens;

a second index projecting optical system for projecting a second index onto a concave surface of the lens, the second index being for a second mode of measurement of radius of curvature of the lens;

a detecting optical system having a photoelectric detecting element for detecting each position of the first index and the second index an optical path of the second index projecting optical system crossing an optical path of the first detecting optical system just short of a concave surface of the lens;

measurement mode changing means for changing the first measurement mode in which the first index is projected onto the lens to the second measurement mode in which the second index is projected onto the lens;

moving means for moving a detecting position of said photoelectric detecting element along an optical axis based on a mode changing signal from said measurement mode changing means; and processing means for determining the refractive power of the lens based on the detected position of the first index and the radius of curvature of the lens based on the position of the second index detected by said photoelectric detecting element.

7. Lens measurement apparatus according to claim 6, wherein said detecting optical system comprises a telecentric diaphragm for detecting the second index and a driving means for inserting the telecentric diaphragm onto the optical path based on the mode changing signal projecting the second index.

8. Lens measurement apparatus according to claim 6, wherein said first index projecting optical system comprises four light sources on a same circle centering the optical axis.

9. Lens measurement apparatus according to claim 6, wherein said second index projecting optical system comprises an optical system for projecting at least three point light sources onto the lens, the point light sources being arranged on a same circle centering the optical axis of the second detecting optical system.

10. Lens measurement apparatus according to claim 6, wherein the photoelectric detecting element of the detecting optical system comprises two-dimensional CCD.

* * * * *